United States Patent
Swedo et al.

(10) Patent No.: US 6,414,137 B1
(45) Date of Patent: Jul. 2, 2002

(54) SELECTIVE SOLVENT EXTRACTION FOR THE PURIFICATION OF PROTECTED NUCLEOSIDES

(75) Inventors: Raymond J. Swedo; Mathias P. Koljack; Romulus Gaita; Stephen Frederick Yates, all of Cook County, IL (US); Charles Wu, Morris County, NJ (US)

(73) Assignee: AlliedSignal Inc., Morristown, NJ (US)

( * ) Notice: Subject to any disclaimer, the term of this patent is extended or adjusted under 35 U.S.C. 154(b) by 0 days.

(21) Appl. No.: 09/440,335

(22) Filed: Nov. 15, 1999

Related U.S. Application Data

(60) Provisional application No. 60/113,724, filed on Dec. 23, 1998.

(51) Int. Cl.$^7$ .......................... C07H 19/00; C07H 1/06
(52) U.S. Cl. .................. 536/27.12; 536/27.1; 536/27.6; 536/27.81; 536/28.5; 536/28.53; 536/28.54
(58) Field of Search ............................ 536/26.73, 26.7, 536/26.8, 27.1, 27.12, 27.6, 27.81, 28.5, 28.53, 28.54

(56) References Cited

U.S. PATENT DOCUMENTS

| | | | |
|---|---|---|---|
| 4,146,454 A | * | 3/1979 | Haber |
| 5,639,867 A | | 6/1997 | Brill |
| 5,811,538 A | * | 9/1998 | Riley et al. |

OTHER PUBLICATIONS

G.S. LI, B.L. Gaffney, R.A. Jones: "Transient protection: efficient one–flask syntheses of protected deoxynucleosides" J. Am. Chem. Soc., vol. 104, 1982, pp. 1316–1319, XP002136167.

J.P. Horwitz, J.A. Urbanski, J. Chua: Nucleosides. II. 5'–0–Mesylthymidine and 3'–0–mesylthymidine J. Org. Chem., vol. 27, 1962, pp. 3300–3302, XP002136168 p. 3301, right–hand column, para. 3.

H. Schaller, G. Weimann, B. Lerch, H. Khorana: "Studies on polynucleotides. XXIV. The stepwise synthesis of specific deoxyribopolynucleotides (4). Protected derivatives of deoxyribonucleosides and new syntheses of deoxyribonucleoside–3'phosphates" J. Am. Chem. Soc., vol. 85, 1963, pp. 3821–3827, XP002136169 cited in the application p. 3823, left–hand col., para. 6 p. 3823, right–hand col., para. 1.

Ti et al., "Transient Protection: Efficient One–Flask Synthesis of Protected Deoxynucleosides," *J.Am. Chem Soc.*, 104, 1316–1319(1982).

Charubala et al., "Nucleotides XXII: Synthesis of Protected 2'–Deoxyribonecleoside–3'–phosphotriesters Containing the —Nitrophenylethyl Phosphate Blocking Group," *Synthesis*, 965 (1984).

Kierzek, "The Synthesis of 5'–)–dimethoxytrityl–N–acyl–2'deoxynucleosides, Improved 'Transient Protection' Approach," *Nucleosides and Nucleotides.*, 4(5), 641–649 (1985).

Schaller et al., *J. Amer. Chem. Soc.*, 85, 3821–3827 (1963).

McGee et al., "A Simple High–Yield Synthesis of $N^2$–(2–Methylepropanoyl)–2'–deoxyguanosine," *Synthesis*, 540 (1983).

\* cited by examiner

*Primary Examiner*—James O. Wilson
(74) *Attorney, Agent, or Firm*—Colleen Szuch

(57) ABSTRACT

A process for the purification of nucleosides, and more particularly to a selective solvent extraction method for purifying protected nucleosides. In the purification process, solid particles of protected nucleosides are selectively washed to remove undesirable polar and/or non-polar impurities, while leaving the solid particles substantially undissolved.

32 Claims, No Drawings

US 6,414,137 B1

SELECTIVE SOLVENT EXTRACTION FOR THE PURIFICATION OF PROTECTED NUCLEOSIDES

REFERENCE TO RELATED APPLICATION

This application claims the benefit of provisional application Ser. No. 60/113,724 filed Dec. 23, 1998, now abandoned.

FIELD OF THE INVENTION

The invention relates to the purification of nucleosides, and more particularly to a selective solvent extraction method for purifying protected nucleosides.

BACKGROUND OF THE INVENTION

Nucleosides are compounds of importance in physiological and medical research, obtained during partial decomposition, i.e., hydrolysis, of nucleic acids, and containing a purine or pyrimidine base linked to either D-ribose (forming ribonucleosides) or D-deoxyribose (forming deoxyribonucleosides). They are nucleotides minus the phosphate group. Well-known nucleosides include adenosine, cytidine, guanosine and thymidine. Nucleosides are multi-functional compounds, having both amino and alcohol functional groups. In order to conduct syntheses selectively and efficiently, it is necessary to block specific functional groups in order to achieve reaction at the desired sites. The "protecting" groups are designed to be removed under specific carefully controlled conditions, usually under relatively mild and typically acidic conditions. To be useful as precursors in the synthesis of high value pharmaceuticals, it is necessary that protected nucleosides be of very high purity (i.e., greater than about 99% by weight (wt %), preferably greater than about 99.5 wt %). The very sensitive nature of the protecting groups together with the variety of polar and non-polar impurities generated during the syntheses of these derivatives makes their purifications complicated, expensive, and difficult to scale-up to industrial scale production.

Typically, the protection of nucleosides involves the derivatization of both amino and alcohol functional groups. An exception is thymidine, which requires only the protection of alcohol groups. Various schemes are employed to achieve these protected nucleosides, but usually the N-protected derivatives (most often N-acylated) are isolated and purified before protecting the alcohol groups. The presence of the free alcohol groups often leaves these derivatives with sufficient polarity that they can be readily purified by recrystallization. However, when these alcohol groups are also derivatized (most often as trityl ethers), the fully protected nucleosides are usually very difficult to crystallize. Purification then is typically achieved by resorting to column chromatography, usually followed by precipitation of the appropriate column fractions into non-solvents to remove traces of co-eluted colored by-products.

Discussions of the synthesis and protection of nucleosides by derivatization may be found in many references, including the following, all of which are incorporated herein by reference. One method of protecting nucleosides is described in Ti, et al., "Transient Protection: Efficient One-flask Syntheses of Protected Deoxynucleosides," *J. Am. Chem. Soc.*, Vol. 104, 1316–1319 (1982), which is discussed in more detail below in regard to the examples. Other methods of synthesizing protected nucleosides are set forth in Charubala, et al., "Nucleotides XXIII: Synthesis of Protected 2'-Deoxyribonucleoside-3'-phosphotriesters Containing the p-Nitrophenylethyl Phosphate Blocking Group," Synthesis 965,(1984). Still other methods for synthesizing such protected nucleosides are set forth in Kierzek, "The Synthesis of 5'-O-dimethoxytrityl-N-acyl-2'-deoxynucleosides, Improved 'Transient 155- Protection' Approach," Nucleosides & Nucleotides, 4(5), 641–649 (1985). In all of these references, protection by N-acylation is effected with benzoyl chloride on adenosine and cytidine derivatives, and with isobutyric anhydride on guanosine derivatives, as is wellknown in the art. The compounds are then further protected by the introduction of methoxytrityl or dimethoxytrityl groups, also as is well-known in the art. An earlier article on the protection of such nucleosides may be found in Schaller, et al., *J. Amer. Chem. Soc.*, Vol. 85, 3821–3827 (1963). Another article on protected nucleosides is McGee, et al., "A Simple High Yield Synthesis of $N^2$-(2-Methylpropanoyl)-2'-deoxyguanosine," Synthesis, 540 (1983). In all of the reported syntheses, the protected nucleosides must be subjected to purification prior to their use in pharmaceutical syntheses.

The impurities generated during the various syntheses of protected nucleosides include polar compounds, such as isobutyric acid and benzamide, and non-polar compounds such as dimethoxytrityl methyl ether and the 3',5'-bis-dimethoxytrityl ether nucleoside derivatives.

On a laboratory scale, recrystallization is widely practiced as a purification method. However, because of the broad range of polarity exhibited by these impurities, purification of protected nucleosides with a single recrystallization solvent system is difficult to achieve. Multiple recrystallizations are often required to achieve required purity levels. As an industrial process, losses (often greater than 10%) of valuable product to the recrystallization medium, and long processing times for mixing, heating, cooling and filtration make this method less attractive.

Column chromatography, especially flash silica gel chromatography, has been used extensively to purify protected nucleosides on a small scale. This method requires the use of large volumes of high purity solvents in proportion to the amount of material purified. The method is also labor-intensive, requiring precise monitoring to make the fraction cuts at the appropriate times to maximize yield of desired product. For these reasons, large-scale use of this method of purification can be very costly.

The equipment required to conduct flash silica gel chromatography on a multi-kilogram scale is expensive to purchase and operate. For example, one commercially available production scale chromatography unit is capable of separating up to about 4 kg of material per run. Run times can vary from 18 to 36 minutes, at an elution rate of 7 liters per minute. The basic unit investment is very expensive, coupled with the cost (and subsequent disposal cost) of 125 to 250 liters of expensive high purity solvent per run. These costs make purification by chromatography unattractive on an industrial scale.

DETAILED DESCRIPTION OF THE INVENTION

In the purification process of the present invention, solid particles of protected nucleosides are selectively washed to remove undesirable polar and/or non-polar impurities, while leaving the solid nucleoside particles substantially undissolved. In a preferred embodiment of the invention, the process comprises two slurry washing steps. In the first slurry washing step, the particles of protected nucleoside are slurried with a solvent for the polar impurities, in which solvent the particles are insoluble or, at most, only slightly soluble. The solid particles are then recovered from the slurry, as by filtering. In the second slurry washing step, the particles are slurried with a solvent for the non-polar impurities, in which solvent the particles are insoluble or, at most, only slightly soluble. The solid particles are then recovered from the slurry, as by filtering. If desired, one or both of the slurry washing steps may be repeated to remove additional impurities. However, preferably each washing is performed only once, to minimize loss of solids. For purposes of this application, particles of protected nucleoside will be considered to be slightly soluble in a solvent when less than about 10 wt % of the total particles dissolve during a washing step, and preferably less than about 5 wt % dissolve, to minimize loss.

While not wishing to be bound to a particular theory of how this process works, it is believed that when the solvent wets and slightly dissolves the surface of the particles, impurities which may be tied up or attached in any manner thereto are released into solution.

Therefore, although it is desirable to minimize the loss of solids, it is believed that improved washing is obtained when at least about 0.1 wt % of the solid particles of protected nucleoside dissolve in the solvent during a washing step, preferably at least about 0.5 wt %.

The washing steps may be done in any order. However, because the polar solvents tend to be less volatile than the non-polar solvents, it is preferred to follow a polar wash with a non-polar wash, in order to minimize the amount of drying needed to remove excess solvent. This is of particular importance when the polar solvent is water-based, because removing water may require extended drying which could affect the nucleoside particles. If only a single washing step is being done, then preferably a non-water based solvent is used.

In another embodiment of the present invention, a single solvent for both the polar and non-polar impurities is used, in which solvent the particles are insoluble or, at most, only slightly soluble. As in the above process, the solid particles of protected nucleoside are then recovered from the slurry, as by filtering. In this case, only one washing step is required, although it may be repeated if necessary or desired. To avoid the problem of removing water by drying, it is preferred that the solvent in a single step washing process contain as little water as possible, preferably none.

As discussed above, protected nucleosides are multifunctional compounds, having both polar and non-polar functionalities, although generally both functionalities are relatively weak. As a result, the protected nucleosides are soluble in some polar and non-polar solvents, but insoluble in others. Some of the impurities which need to be removed are soluble in solvents in which the protected nucleosides are not soluble. It is simple to remove such impurities by slurry washing, because they can be solubilized without dissolving the protected nucleoside particles. On the other hand, some of the impurities, particularly intermediates or partially reacted nucleoside materials, are only soluble in the same solvents, either polar or non-polar, in which the protected nucleosides are soluble. To dissolve these materials it is necessary to use a solvent which can also dissolve the protected nucleoside particles. The present inventors have found that by mixing a solvent in which a protected nucleoside is soluble with a solvent in which it is insoluble, one can obtain a slurry washing solvent which dissolves the impurities which need to be removed while only dissolving a small amount of the protected nucleoside.

Therefore, in accordance with one embodiment of the present invention, polar impurities are removed from particles of a protected nucleoside by using a mixture of miscible polar solvents, wherein the protected nucleoside is soluble in one of the solvents and substantially insoluble in the other. The solvents need to be ones which otherwise do not affect or react with the protected nucleosides.

A particularly preferred combination of polar solvents is water and acetonitrile.

While protected nucleosides are relatively insoluble in water, particularly cold water, they are highly soluble in acetonitrile. The most effective ratio of acetonitrile to water to use for the purification of a specific protected nucleoside will be a function of the protecting groups used. The optimum ratio is readily determined by a series of experiments in which very small amounts of crude product are slurried with small volumes of solvents, then the filtrates analyzed by HPLC analysis. Any ratio of acetonitrile and water may be used, provided the desired slurry washing is obtained. Preferably the ratio of acetonitrile to water is within the range of about 5:95 to about 30:70, by volume, more preferably from about 10:90 to about 25:75. Such mixtures of acetonitrile in water will effect substantial removal of the polar impurities while removing very little of the protected nucleoside. Other polar solvents which can be used in combination with water include lower molecular weight, i.e., $C_1$ to $C_6$, linear and branched alcohols, including methanol, ethanol, isopropanol, propanol and butanol; dipolar aprotic solvents such as dimethylformamide (DMF), N-methylpyrrolidone, and dimethyl sulfoxide (DMSO); and acetone.

In like manner, non-polar impurities can be removed from particles of a protected nucleoside by using a mixture of miscible non-polar solvents, wherein the protected nucleoside particles are soluble in one of the solvents, and substantially insoluble in the other. As with the polar solvents, the non-polar solvents need to be ones which otherwise do not affect or react with the protected nucleosides.

In accordance with a preferred embodiment of the present invention, the non-polar impurities can be removed with mixtures of hexane and methylene chloride. The protected nucleosides are effectively insoluble in hexane, but they are highly soluble in methylene chloride. A suitable ratio of hexane to methylene chloride to use for the purification of a specific protected nucleoside will be a function of the particular nucleoside and the protecting groups used, as well as the nature of the impurities present. This can readily be determined by one skilled in the art by a series of small scale experiments as described above for the removal of polar by-products. Any ratio of hexane to methylene chloride may be used, provided the desired slurry washing is obtained. However, preferably, the ratio of hexane to methylene chloride is within the range of about 3:1 to about 1:3, by volume, and more preferably within the range of about 3:1 to about 1:1. Typically, a volume ratio of about two parts hexane to one part methylene chloride will effect the removal of the non-polar by-products while removing very little of the protected nucleoside. Cyclohexane may be used instead of, or in combination with, hexane in these formulations. Non-polar solvents in which protected nucleosides generally are insoluble include $C_5$ to $C_{10}$ linear, branched and cyclic hydrocarbons. Non-polar solvents in which protected nucleosides generally are soluble include ethyl acetate, and chlorinated solvents such as methylene chloride, chloroform, carbon tetrachloride and dichloroethane.

In accordance with another embodiment of the present invention, both polar and non-polar impurities may be removed in a single step by using a mixture of polar and non-polar solvents. The solvent mix must be one in which the product particles are insoluble or, at most only slightly soluble, and the polar and non-polar impurities are soluble. Generally, this is achieved by using a mixture of solvents which are miscible together and capable of dissolving the polar and/or non-polar impurities which are present. Preferably the mixture contains at least one polar and one non-polar solvent. If needed, a third solvent may be used which is miscible with both of the other solvents, to form a three component mixture. This third solvent can be a bifunctional solvent which is miscible with both the polar and the non-polar solvents. It is preferred to avoid using water in such a mixture, to reduce the amount of drying needed after filtration. It is preferred to use an alcohol as the polar solvent in a single step process, with methanol particularly preferred. A suitable mixture of solvents is methanol, in combination with the non-polar solvent mixture of hexane and methylene chloride. Good results were obtained using a mixture of about 80% hexane, with about 10% methanol and about 10% methylene chloride. The mixture of solvents can then be adjusted to maximize the removal of the particular impurities and minimize the loss of nucleoside, as discussed above.

The purification process of the present invention may be used to purify any protected nucleoside. It is particularly useful for purifying nucleosides which are difficult to purify by recrystallization. As discussed above, nucleosides which are protected by derivatization of both amino and alcohol functional groups may lack sufficient polarity to be readily purified by recrystallization. The process is particularly suitable for purifying protected nucleosides in which the alcohol group has been derivatized as a trityl ether, and the amino group has been derivatized as a benzoyl or isobutyryl group. Such nucleosides include adenosine, cytidine and guanosine, and has been found particularly useful for adenosine and guanosine. Thymidine is generally protected only by derivatization of its alcohol groups and, therefore, still has sufficient polarity to be purified by recrystallization. However, the slurry washing process of the present invention is also suitable for the purification of thymidine. It is believed that the slurry washing process is simpler, uses less solvent, and retains more nucleoside than recrystallization. One skilled in the art can readily determine whether the slurry washing purification process of the present invention is suitable for use in purifying other particular protected nucleosides.

In the following examples, protected deoxynucleosides are synthesized according to the procedures described by Ti, et al., "Transient Protection: Efficient One-flask Syntheses of Protected Deoxynucleosides," J. Am. Chem. Soc., Vol. 104, 1316–1319 (1982), incorporated herein by reference. The reference describes an application of the concept of transient protection to the synthesis of protected deoxynucleosides. The deoxynucleosides are first treated with trimethylchlorosilane in pyridine for protection of the hydroxyl groups. Then the product is immediately reacted with an acylating group, benzoyl. chloride for deoxyadenosine and deoxycytidine, and isobutyric anhydride for deoxyguanosine, to effect N-acylation. Hydrolysis of the trimethylsilyl groups takes a few hours in aqueous pyridine or a few minutes with dilute ammonia. The ammonia also effects selective hydrolysis of the initially formed N,N-dibenzoyldeoxyadenosine derivative to the desired N-benzoyldeoxyadenosine. This one-flask procedure is described as giving crystalline N-acyl deoxynucleosides of deoxyadenosine and deoxycytidine in 95% yield and deoxyguanosine in 75% yield, in only a few hours. The 5'-O-dimethoxytrityl deoxynucleosides are also obtained in the one-flask procedure by initial reaction of the deoxynucleosides with 4,4'-dimethoxytrityl chloride, followed by treatment with trimethylchlorosilane and then reaction with the acylating group, benzoyl chloride. After simple purification by flash chromatography, the deoxyadenosine and deoxycytidine products are each obtained in 80–90% yield. This same process can be used to form the 5'-O-dimethoxytrityl deoxyguanoside, using isobutyric anhydride as the acylating group.

EXAMPLES

Comparative Example 1

Purification of $N^6$-Benzoyl-5'-O-(4,4'-dimethoxytrityl)-2'-deoxyadenosine by Conventional Methods $N^6$-benzoyl-5'-O-(4,4'-dimethoxytrityl)-2'-deoxyadenosine (hereinafter "protected adenosine") was synthesized on a 0.1 mole scale according to the procedure described by Ti, et al. The yield of crude product after precipitation from ethyl acetate into cyclohexane was 59.2 grams (90% crude yield). HPLC analysis showed the crude product to contain 54% protected nucleoside, 22.6% total polar impurities, and 23.3% total non-polar impurities.

The first step in the purification of the crude protected nucleoside was chromatographic separation on a 4×10 cm silica gel column. The column was eluted sequentially with 600 mL of $CH_2Cl_2$, 300 mL of $CH_3OH$, and finally with 200 mL of $CH_3CN$. By combining the appropriate column fractions and evaporating the solvents, 33.0 grams of purified protected nucleoside were obtained. HPLC analysis showed a purity of 63.7%, with a total of 11.1% of polar impurities, and total of 25.3% of non-polar impurities.

Recrystallization of the protected nucleoside obtained from column chromatography from 75 mL of isopropanol gave 31.6 grams of product. HPLC analysis gave a purity of 73.5%, with a total of 8.2% polar impurities, and a total of 18.4% of non-polar impurities.

A second recrystallization from 1 L of hexane:$CH_2Cl_2$ (1:1, by volume) gave a yield of 20.5 grams of product having a purity of 98.28%, with a total of <0.1% of polar impurities, and a total of 1.7% of non-polar impurities.

A final recrystallization from 500 mL of hexane: $CH_2C_2$ (2:1, by volume), followed by drying under vacuum with a nitrogen bleed at 35° C., gave 18.8 grams (28.6% overall yield) of purified protected nucleoside. HPLC analysis showed a purity of >99.8%, with <0.1% of polar impurities, and <0.1% of non-polar impurities.

Overall, on a per mole basis, purification of this protected nucleoside by this comparative example of a present conventional method would require more than 27 liters of solvent, while only producing a 28.6% overall yield.

Example 2

Purification of $N^6$-Benzoyl-5'-O-(4,4'-dimethoxytrityl)-2'-deoxyadenosine by the Slurry Washing Method of the Present Invention The indicated protected nucleoside was synthesized on a 0.05 mole scale according to the procedure described by Ti, et al. The yield of crude product after precipitation from $CH_2Cl_2$ into cyclohexane:ether (2:1, by volume) was 23.4 grams (90.2% yield). HPLC analysis showed a purity of 92.73%, with a total of 2.71% of polar impurities, and a total of 4.57% of non-polar impurities.

To remove the non-polar impurities, the crude product was slurried twice with 150 mL portions of hexane:$CH_2Cl_2$ (2:1, by volume). Each slurry washing was conducted at room temperature for about 30 minutes. HPLC analysis of the filtrates from the slurries showed that they contained a total of 1.4% of polar impurities, 94.7% of non-polar impurities, and only 3.8 % of protected nucleoside.

To remove the polar impurities, the above product was slurried with 300 mL of 30 volume % $CH_3CN$ in $H_2O$ at room temperature for 30 minutes, followed by filtration and slurrying with 100 mL of 20 volume % of $CH_3CN$ in H2O at room temperature for 30 minutes. HPLC analysis of the filtrates from the slurries showed that they contained a total of 94.3% of polar impurities, 1.4% of non-polar impurities, and only 4.2% of protected nucleoside.

After drying under vacuum at 35° C. with a nitrogen bleed, the final yield of purified protected nucleoside was 19.2 grams (74% overall yield). HPLC analysis showed a purity of 99.61%, with a total of 0.39% of polar impurities, and <0.01% of non-polar impurities.

Overall, on a per mole basis, purification of this protected nucleoside by this method would require a total of only 7 liters of solvent. This is a substantial savings over the conventional method of column chromatography and recrystallizations, as set forth in Comparative Example 1.

Example 3

Purification of $N^2$-isobutyryl-5'-O-(4,4'-dimethoxytrityl)-2'-deoxyguanosine by the Slurry Washing Method of the Present Invention The indicated protected nucleoside was synthesized according to the procedure described by Ti, Gaffney and Jones (see above). HPLC analysis of the crude protected nucleoside, as isolated, showed a purity of 92.7%, with a total of 4% of polar impurities, and a total of 3.2% of non-polar impurities.

The non-polar impurities were removed from the crude protected nucleoside product by slurrying the product twice with 150 mL portions of hexane:$CH_2Cl_2$ (2:1, by volume). Each slurry washing was conducted at room temperature for 30 minutes. HPLC analysis of the filtrates from the slurry washings showed that they contained a total of <0.1% of polar impurities, >99.8% of non-polar impurities, and <0.1% of protected nucleoside.

The polar impurities were then removed the above-treated protected nucleoside product by slurrying it two times with 150 mL portions of 25 volume % $CH_3CN$ in $H_2O$. Each slurry washing was conducted at room temperature for 1 hour. HPLC analysis of the filtrates from the slurry washings showed that they contained a total of 51% of polar impurities, <0.1% of non-polar impurities, and 49% of protected nucleoside.

While the slurry washing method was successful here in purifying the crude protected nucleoside, it is believed that the $CH_3CN$:$H_2O$ mixture used to remove the polar impurities here was not optimized. Therefore, the slurry washing filtrates contained high levels of protected nucleoside. This illustrates the need to tune the proportions to the particular nucleoside undergoing purification. In this case, $H_2O$ to $CH_3CN$ proportions of 80:20, or even 90:10 would have resulted in removal the polar impurities without removing as much of the protected nucleoside product.

Example 4

Purification of 5'-O-Dimethoxytritylthymidine

One of the impurities present in a synthesized sample of the protected nucleoside 5'-O-dimethoxytritylthymidine was a pink to purple colored material of unknown composition. The impurity was found to have a high polarity, and to be soluble in a variety of polar solvents, such as water, methanol, dimethylformamide (DMF) and acetonitrile. Thus, it appeared to be removable by slurry extraction using these solvents or mixtures of these and other less polar solvents. The ideal solvent systems for this treatment are those capable of selectively dissolving the colored impurity, but not the protected nucleoside. The solvents preferably should have high volatility, so they can be readily removed, as by vacuum drying, after the treatment. Thus, water; a mixture of methanol and hexane (about 5% methanol, by volume); and a mixture of water and acetonitrile (about 20–80% water, by volume) were believed to be suitable solvent systems.

Example 4A

A 2.00 g sample of 5'-O-dimethoxytritylthymidine containing the pink colored impurity was mixed with 10 g of deionized water, and the mixture stirred for 30 minutes. The mixture was then filtered. The filter cake was white, and the mother liquor was pink. HPLC analysis showed no detectable polar impurities. Upon drying, the filter cake weighed 1.95 g, showing a recovery yield of 97.5%.

Example 4B

A 25.0 g sample of 5'-O-dimethoxytritylthymidine containing the pink colored impurity was mixed with 200 mL of methanol-hexane mixture (5% methanol), and the mixture was stirred for 30 minutes. The mixture was then filtered. The filter cake was white, and the mother liquor was pink. HPLC analysis showed no detectable polar impurities. Upon drying, the filter cake weighed 24.8 g, showing a recovery yield of 99.2%.

Example 4C

A 701 g batch of 5'-O-dimethoxytritylthymidine containing the pink colored impurity was placed in a four-liter beaker. To this beaker was added 2 liters of a mixture comprising 1600 mL of hexane, 200 mL of methanol and 200 mL of methylene chloride. The resulting suspension was stirred with a wooden spoon until it was homogeneous. Then the mixture was allowed to settle (approximately two minutes), and the pink liquid supernatant was filtered with suction.

An additional 1 liter of solvent mixture with the same proportions as those indicated above was added to the solid remaining in the beaker, and stirred again. Then the entire contents of the beaker were filtered using the same device used earlier. A final 1 liter of solvent mixture was used to rinse the beaker, and then also transferred to the filter funnel. Suction was applied to the funnel until no more liquid filtrate could be obtained.

The resulting product was dried in a vacuum oven. After drying, it was white in color, and had a purity by HPLC of greater than 99%.

We claim:

1. A method for purifying a composition comprising solid particles of a protected nucleoside and polar and non-polar impurities, the method comprising:
   a) applying a solvent in which the polar impurities are soluble and in which the particles of protected nucleoside are at most slightly soluble; and
   b) applying a solvent in which the non-polar impurities are soluble and in which the particles of protected nucleoside are at most slightly soluble, wherein steps (a) and (b) may be performed in any order.

2. The method of claim 1 wherein said solvent for the polar impurities comprises a mixture of miscible first and second polar solvents, wherein the particles of protected nucleoside are soluble in the first-polar solvent, and relatively insoluble in the second polar solvent.

3. The method of claim 2 wherein said first polar solvent is selected from the group consisting of acetonitrile, $C_1$ to $C_6$ linear and branched alcohols, dimethylformamide, dimethyl sulfoxide, acetone and mixtures thereof, and said second polar solvent is water.

4. The method of claim 3 wherein said first polar solvent is acetonitrile.

5. The method of claim 4 wherein the ratio of acetonitrile to water is within the range of about 5:95 to about 30:70 by volume.

6. The method of claim 1 wherein said solvent for non-polar impurities comprises a mixture of miscible first and second non-polar solvents, wherein the particles of protected nucleoside are highly soluble in the first non-polar solvent, and relatively insoluble in the second non-polar solvent.

7. The method of claim 6 wherein said first non-polar solvent is selected from the group consisting of chlorinated solvents, ethyl acetate and mixtures thereof, and said second non-polar solvent is selected from the group consisting of $C_5$ to $C_{10}$ linear, branched and cyclic hydrocarbons and mixtures thereof.

8. The method of claim 7 wherein said chlorinated solvents are selected from the group consisting of methylene chloride chloroform, carbon tetrachloride, dichloroethane and mixtures thereof.

9. The method of claim 7 wherein said first non-polar solvent is methylene chloride.

10. The method of claim 7 wherein said second non-polar solvent is hexane or cyclohexane.

11. The method of claim 7 wherein said first non-polar solvent is methylene chloride and said second non-polar solvent is hexane.

12. The method of claim 11 wherein the ratio of methylene chloride to hexane is within the range of about 3:1 to about 1:3, by volume.

13. The method of claim 12 wherein the ratio of methylene chloride to hexane is about 1:2, by volume.

14. The method of claim 1 wherein the nucleoside which is protected is selected from the group consisting of deoxyadenosine, deoxycytidine, deoxyguanosine and thymidine.

15. The method of claim 1 wherein the nucleoside includes amino and alcohol functional groups, and protection involves derivatization of the amino and alcohol groups.

16. The method of claim 15 wherein the alcohol group is derivatized as a trityl or dimethoxytrityl ether.

17. The method of claim 15 wherein the amino group is derivatized as a benzoyl or isobutyryl group.

18. The method of claim 15 wherein the protected nucleoside is selected from the group consisting of $N^6$-benzoyl-5'-O-(4,4'-dimethoxytrityl)-2'-deoxyadenosine and $N^2$-isobutyryl-5'-O-(4,4'-dimethoxytrityl)-2'-deoxyguanosine.

19. The method of claim 1 wherein step (a) is performed before step (b).

20. The method of claim 1 farther comprising recovering purified particles of protected nucleoside.

21. The method of claim 20 wherein said recovering comprises filtering from the purified particles from the solvent of the last applying step.

22. The method of claim 21 further comprising evaporating the solvent from the filtered particles.

23. A method for purifying a composition comprising solid particles of a protected nucleoside and impurities, the method comprising applying a solvent in which the impurities are soluble and in which the particles of protected nucleoside are at most slightly soluble.

24. The method of claim 23 in which the impurities comprise polar and non-polar impurities.

25. The method of claim 24 wherein said solvent comprises a mixture of a polar solvent and a non-polar solvent.

26. The method of claim 25 wherein said solvent further comprises a solvent which is miscible with both the polar and non-polar solvents.

27. The method of claim 26 wherein said solvent comprises hexane, methanol and methylene chloride.

28. The method of claim 23 wherein the nucleoside which is protected is selected from the group consisting of deoxyadenosine, deoxycytidine, deoxyguanosine and thymidine.

29. The method of claim 28 wherein the solvent comprises water.

30. The method of claim 28 wherein the solvent comprises water and acetonitrile.

31. The method of claim 28 wherein the solvent comprises methanol and hexane.

32. The method of claim 28 wherein the solvent comprises hexane, methanol and methylene chloride.

* * * * *